United States Patent
DeLong et al.

(10) Patent No.: US 9,977,016 B2
(45) Date of Patent: May 22, 2018

(54) TWO-DIMENSIONAL FLUORESCENCE DIFFERENCE SPECTROSCOPY CHARACTERIZATION OF NANOPARTICLES AND THEIR INTERACTIONS

(71) Applicant: Kansas State University Research Foundation, Manhattan, KS (US)

(72) Inventors: Robert DeLong, Manhattan, KS (US); Miranda Hurst, Rogersville, MO (US)

(73) Assignee: Kansas State University Research Foundation, Manhattan, KS (US)

( * ) Notice: Subject to any disclaimer, the term of this patent is extended or adjusted under 35 U.S.C. 154(b) by 27 days.

(21) Appl. No.: 15/344,150

(22) Filed: Nov. 4, 2016

(65) Prior Publication Data

US 2017/0131272 A1     May 11, 2017

Related U.S. Application Data

(60) Provisional application No. 62/251,488, filed on Nov. 5, 2015.

(51) Int. Cl.
  *G01N 33/543*     (2006.01)
  *G01N 21/64*      (2006.01)
  *C12Q 1/68*       (2018.01)

(52) U.S. Cl.
  CPC ......... *G01N 33/54346* (2013.01); *C12Q 1/68* (2013.01); *C12Y 113/12007* (2013.01); *C12Y 302/01023* (2013.01); *G01N 21/6428* (2013.01); *G01N 2021/6421* (2013.01)

(58) Field of Classification Search
  CPC .............................. G01N 33/543; G01N 21/64
  USPC .............................................. 436/86, 94, 172
  See application file for complete search history.

(56) References Cited

U.S. PATENT DOCUMENTS

| | | | | |
|---|---|---|---|---|
| 6,080,584 A * | 6/2000 | Alfano | ............... | G01N 21/6456 422/82.08 |
| 6,232,608 B1 * | 5/2001 | Giebeler | ............ | G01N 21/6452 250/458.1 |
| 6,236,456 B1 * | 5/2001 | Giebeler | ............ | G01N 21/6452 250/458.1 |
| 6,313,471 B1 * | 11/2001 | Giebeler | ............ | G01N 21/6452 250/458.1 |
| 6,316,774 B1 * | 11/2001 | Giebeler | ............ | G01N 21/6452 250/458.1 |
| 6,721,582 B2 * | 4/2004 | Trepagnier | ........... | A61B 5/0059 600/316 |

(Continued)

OTHER PUBLICATIONS

Kitagaki, H. et al, Natural Science Report, Ochanomizu University 1985, 36, 89-102.*

(Continued)

Primary Examiner — Arlen Soderquist
(74) Attorney, Agent, or Firm — Hovey Williams LLP

(57) ABSTRACT

Methods of characterizing nanoparticles, nanoparticle complexes, and their biomolecular interactions are provided. Concurrent excitation and emission wavelength scans are performed and the optimal fluorescence intensity for the intersect of these wavelengths is determined. The intersect is dependent upon the physical characteristics of the particle and can be used to verify, for example, attachment of biomolecules, amount of biomolecules present, and structure of the attached biomolecule.

24 Claims, 12 Drawing Sheets
(9 of 12 Drawing Sheet(s) Filed in Color)

(56) References Cited

U.S. PATENT DOCUMENTS

| | | | | |
|---|---|---|---|---|
| 8,723,139 | B2* | 5/2014 | Stock | G01J 3/0264 250/458.1 |
| 2002/0016534 | A1* | 2/2002 | Trepagnier | A61B 5/0059 600/316 |
| 2002/0043651 | A1* | 4/2002 | Darrow | G01N 33/582 252/408.1 |
| 2005/0084890 | A1* | 4/2005 | Turchi | C12Q 1/6886 435/6.18 |
| 2007/0031336 | A1* | 2/2007 | Auberson | C07D 513/14 424/9.6 |
| 2009/0099045 | A1* | 4/2009 | Jackson | C40B 50/18 506/32 |
| 2010/0277725 | A1* | 11/2010 | Zimenkov | G01J 3/10 356/325 |
| 2012/0108459 | A1* | 5/2012 | Jackson | C40B 50/18 506/9 |
| 2012/0259187 | A1* | 10/2012 | Kruijt | A61K 31/409 600/317 |
| 2012/0313010 | A1* | 12/2012 | Stock | G01J 3/0264 250/459.1 |

OTHER PUBLICATIONS

Kitagaki, H. et al, Journal of Biochemistry 1985, 98, 385-393.*
Tendian, S. W. et al, Biochemistry 1995, 34, 6464-6474.*
Youvan, D. C. et al, Biotechnology et alia, 1997 <www.et-al.com> 1:1-16.*
Rogers, D. P. et al, Biochemistry 1998, 37, 11714-11725.*
Park, S. et al, Biochemistry 2000, 39, 11732-11741.*
Sun, W. et al, Journal of Luminescence 2009, 129, 778-783.*
Comley, J., Drug Discovery World 2012, Fall, 23-45.*

* cited by examiner

FIG. 9

- ● ZnO + 50 μg/mL RBD
- ○ ZnO + 25 μg/mL RBD
- ◌ ZnO + 37.5 μg/mL RBD

TWO-DIMENSIONAL FLUORESCENCE DIFFERENCE SPECTROSCOPY CHARACTERIZATION OF NANOPARTICLES AND THEIR INTERACTIONS

CROSS-REFERENCE TO RELATED APPLICATION

The present application claims the benefit of U.S. Provisional Patent Application No. 62/251,488, filed Nov. 5, 2015, which is incorporated by reference herein in its entirety.

FEDERALLY SPONSORED RESEARCH OR DEVELOPMENT

This invention was made with government support under Grant No. 2R15CA139390-02 awarded by the National Institute of Health. The government has certain rights in the invention.

BACKGROUND OF THE INVENTION

Field of the Invention

The present invention is generally directed toward methods of characterizing nanoparticles, particularly nanoparticle complexes comprising an organic species such as a biomolecule or pharmaceutical compound. In certain embodiments, the present invention utilizes two-dimensional fluorescence difference spectroscopy in order to generate a unique identifier or "fingerprint" for the particular nanoparticle or nanoparticle complex that can be used to characterize the nanoparticle or nanoparticle complex.

Description of the Prior Art

In the last 10-15 years, nanotechnology has emerged as an area of great interest in the fields of physics and chemistry. While great numbers of various types of nanoparticles have been synthesized, including elemental nanoparticles and nanoparticle compounds and composites, and the physiochemical properties of these nanoparticles are fairly well understood, there exists a fundamental, if not disturbing, gap regarding the understanding of the biochemical and biological activities of these nanomaterials. In particular, there is a lack of understanding of the effect that many nanomaterials have on the structure-function of nucleic acids and proteins, cell metabolism, and cell signaling.

Due to this lack of understanding, many areas of nanomaterial research stand at an impasse. Materials originally thought to be inert are not. For example, despite the fact that earth's organisms are carbon-based, there is an alarming and steadily growing literature that suggests that carbon nanotubes (CNTs) can be quite toxic to cells and tissues. This seems to shadow, if not plague, many of the first generation nanomaterials that were studied including, but not limited to, silicon dioxide, quantum dots and others.

Nanoparticles have been proposed as platforms for delivery of various therapeutic materials, such as proteins and nucleic acids, into a human or animal body or as biosensors. In order to effectively design nanomaterials for these and other applications, it is necessary to develop a quantitative understanding of how nanoparticles perform and behave in the biological environment. More specifically, to study the important nanobio interface, it is necessary to have a means of quantifying the nanoparticle surface in such a way as biomolecular interaction could be directly detected.

Current methods of characterizing the structure of nanoparticle complexes include electron microscopy, dynamic laser light scatter, zeta potential analysis, and traditional fluorescence and absorbance spectral analyses, which require multiple techniques and data to piece together the information needed. Thus, these current methods of characterizing nanoparticle complexes are quite time intensive and may be insufficient to adequately characterize the particles. Accordingly, there is a need for methods of accurately characterizing nanoparticles and their biomolecular complexes more quickly, more simply, and quantitatively.

SUMMARY OF THE INVENTION

According to one embodiment of the present invention there is provided a method of detecting the attachment of an organic species onto the surface of one or more nanoparticles within a sample comprising the nanoparticles and the organic species. The method comprises performing concurrent scans of both fluorescence excitation and emission wavelengths for the nanoparticles within the sample and then determining the intersect between the excitation and emission wavelengths yielding the highest fluorescence intensity. The intersect indicates the presence or absence within the sample of a nanoparticle complex comprising the one or more nanoparticles having the organic species attached to the surface of the nanoparticle.

According to another embodiment of the present invention there is provided a method of quantifying the attachment of an organic species onto the surface of one or more nanoparticles forming a nanoparticle complex. The method comprises performing concurrent scans of the fluorescence excitation and emission wavelengths for the nanoparticle complex and then determining the intersect between the excitation and emission wavelengths yielding the highest fluorescence intensity. Next, the intersect is compared to one or more known standards for the nanoparticle complex to determine an amount of the organic species that is attached to the nanoparticle.

According to yet another embodiment of the present invention there is provided a method of detecting changes in the structure of a biomolecule associated with attachment of the biomolecule to a nanoparticle thereby forming a nanoparticle complex. The method comprises performing concurrent scans of the fluorescence excitation and emission wavelengths for the biomolecule in comparison to the nanoparticle complex and then determining the intersect between the excitation and emission wavelengths yielding the highest fluorescence intensity. The intersect is compared to one or more known standards observing the change in the biomolecule's intrinsic fluorescence to detect changes in the biomolecule structure occurring during attachment to the nanoparticle. In certain embodiments, the technique extends to the ability to detect structural or conformational changes to biomolecules upon their interaction with the nanoparticle, assuming that the biomolecule harbors intrinsic or extrinsic fluorescence. Further, the on-particle real-time analysis provided can be used to confirm binding, but fluorescence intensity changes that occur also can be used to provide a means of rapidly quantifying particle-associated payload of an organic species, such as a biomolecule, drug, or vaccine.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 9 is a comparative plot of excitation and emission wavelengths at peak intensity showing spectral signature shift upon ZnO NP interaction with Ras-Binding domain (RBD) peptide at varying concentrations.

DETAILED DESCRIPTION OF THE PREFERRED EMBODIMENT

Figure 1A:
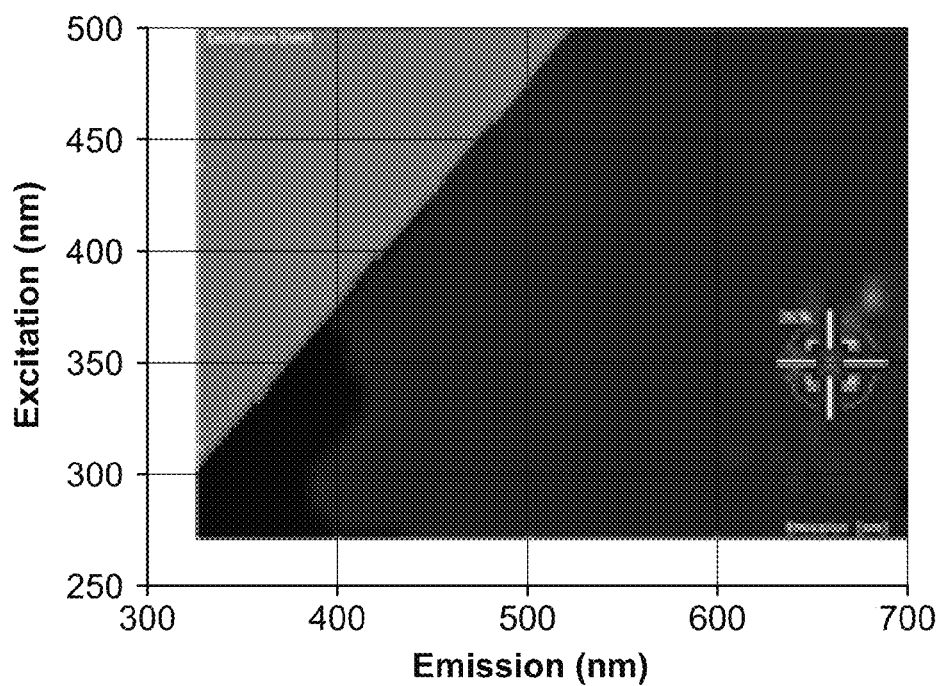
FIG. 1a is a 2D-FDS heat map for ZnO nanoparticle.

When light of sufficient energy (E>Eg) is incident on a material, photons are absorbed and electrons become excited, moving the electrons from the valence band to the conduction band leaving behind holes. Some of the absorbed energy is lost to vibration; however, radiative relaxation results in the emission of fluorescent light as the electron returns to its ground state. Fluorescence emission is thus a result of the band gap in semi-conductor materials, or the difference in energy between the valence band and the conduction band. This is specifically important as the continuous energy band gap breaks down further into discrete energy levels at the nanoscale. These discrete energy levels can provide unique properties that are not observable macroscopically. Further, the band gap is related to the particle size, where an increase in the band gap occurs as the particles approach quantum confinement. Upon electrostatic interaction, the optical properties within the nanomaterial change, resulting in a shift in the peak fluorescence excitation and emission wavelengths, or spectral signature.

Two-dimensional fluorescence difference spectroscopy (2D-FDS) can be used to concurrently scan both the excitation and emission wavelengths of a subject material to determine the intersect of these wavelengths yielding the highest intensity (in relative light units). It has been discovered that this technique can detect a nanoparticle's signature fluorescent fingerprint. As various compounds and chemical species are attached to the nanoparticle's outer surface, it has been discovered this fluorescent fingerprint shifts. For example, when biomolecules, such as ribonucleic acid (RNA) and protein, are loaded onto the surface of the nanoparticle, the optimal fluorescent excitation and emission intersect generated by 2D-FDS shifts thereby indicating association of the nanoparticle and the biomolecule. The decrease in intensity, or fluorescence quenching, is another indication of interaction, and may be used to quantify the degree of loading of the biomolecule onto the surface of the nanoparticle. When analyzing the 2D fluorescence of the RNA or protein, as opposed to the nanoparticle, the change in optimal fluorescence can lend insight into changes in the structure of the biomolecule. For example, a deviation in folded structure can alter a functional site and yield a nonfunctional biomolecule. Therefore, 2D-FDS can also be used to identify structural changes within the attached biomolecule that would ultimately affect the biomolecule's function, for example, within a biosensor or pharmaceutical application.

By using 2D-FDS to concurrently scan the optimal excitation and emission wavelengths, as well as fluorescence intensity, for the nanoparticle the need for extensively gathering several independent spectra is eliminated. While other scanning means, such as electron microscopy, can be used to visualize, for example, the protein or RNA corona interaction on the nanoparticle surface and give the particle size, they do not provide quantitative information regarding the electronic state of the nanoparticle surface and its structural rearrangement or alteration in electrical charge with local interaction, which is measurable by fluorescence. The electronic characteristics of the nanoparticle are changed by the introduction of an organic species, such as a biomolecule thereby ultimately affecting the fluorescence properties of the nanoparticle. From this information, a more direct characterization of the nanoparticle/biomolecule complex can be achieved.

Methods according to certain embodiments of the present invention can be used in a broad range of commercial applications. In particular embodiments, methods according to the present invention can be used in quality assurance applications to validate and quantify drug or biomolecule loading onto nanoparticles prior to distribution as this technique can be performed in high throughput screening. In other embodiments, the methods can be used to confirm biomolecule association to a nanoparticle in nanoparticle complexes, such as nanoparticle-RNA/protein complexation for biosensing or drug delivery. In still other embodiments, given the extreme sensitivity of 2D-FDS, the methods may be used to discriminate subtle differences in ultra-structure or surface interactions, which can be used to indicate biochemical or biological activity of nanocomplexes of nanoparticles and biomolecules.

As noted above, certain embodiments of the present invention can be used to detect attachment of an organic species onto the surface of one or more nanoparticles within a sample to be tested. The organic species may be any organic compound, molecule, or polymer; however, biomolecules, such as proteins, protein enzymes, nucleic acids (DNA, RNA, oligonucleotide, aptamers), various pharmaceutical compounds, surface functionalization molecules, and combinations thereof are particularly preferred. In particular embodiments the organic species comprises a member selected from the group consisting of B-Galactosidase, Luciferase, reverse transcriptase enzymes, deoxyribonuclease, polyinosinic-polycytidylic acid RNA, RNAse, protamine sulfate, Ras binding domain (RBD) peptide, splice switching oligonucleotide (SSO), torula yeast RNA, polyethylene glycol (PEG), glycol chitosan, and polyacrylic acid (PAA). In certain embodiments, the organic species may be a polymer that is applied to the nanoparticle as a coating. In such embodiments, the organic species at least partially coats the nanoparticle.

The nanoparticle to which the organic species is attached, or at least is intended to attach, can be any ultrafine particle having an average particle diameter of less than 500 nm, and is preferably between about 1 to about 100 nm in diameter. In particular, the nanoparticle is non-toxic and suitable for being administered to a human or animal. It has been discovered that a wide range of materials can be analyzed by 2D-FDS and unique fluorescent fingerprints can be generated therefor. In certain embodiments, the nanoparticle comprises a member selected from the group consisting of metal oxides, elemental metals, and combinations deriving composites thereof. In particularly preferred embodiments, the nanoparticle is selected from the group consisting of the lanthanides, ZnO, ZnS doped Mn, ZnS doped Fe, MgO, MnO, CoO, $Si_3N_4$, CSi, $B_4C$, NiO, Ni/NiO, Ni/ZnO, Co/ZnO, Au, FeO, and $Fe_2O_3$.

In certain embodiments, the nanoparticle comprises an upconversion nanoparticle or "upconverter". Up-converters may comprise lanthanide-doped nanoparticles that tend to fluoresce or luminesce more in the near infrared range (NIR), and may be particularly suitable to serve as nanosensors under biological conditions in that they do not interfere with the indigenous fluorescent molecules in cells and tissues. Like the other nanoparticles discussed herein, upconverters give a unique 2D-FDS pattern that can be used to detect the binding of RNA molecules as well as RNA oligonucleotide chemistries. In certain embodiments, the upconverters comprise $Y_2O_3$ nanocrystals doped with $Yb^{3+}$, $Er^{3+}$, $Ho^{3+}$, and/or $Tm^{3+}$. The doping of these nanocrystals with Yb3+ as a sensitizer makes excitation possible upon application of light in the near infrared range to obtain red, green, and blue emissions. Doped rare earth nanocrystals can be synthesized according to a number of methods, such as coprecipitation, solution combustion, hydrothermal processes, sol-gel, colloidal solutions, flame synthesis, and vapor phase synthesis. Vapor phase synthesis of these upconversion nanoparticles is discussed in Glaspell et al., J. Phys. Chem. C 112, 11527-11531 (2008), which is incorporated by reference herein in its entirety.

Concurrent scans of the fluorescence excitation and emission wavelengths are performed. As used herein, the term "concurrent" can mean performed simultaneously, performed successively or sequentially without interruption in between the various scans. Preferably, the scans are performed using two-dimensional fluorescence difference spectroscopy, such as the Spectramax i3x 2D-FDS instrument from Molecular Devices. In one particular embodiment, the sample to be tested is prepared by dispersing or suspending the nanoparticle sample within a liquid medium, such as spectral grade water, and then placed within the spectroscope. For each excitation wavelength, the instrument consecutively scans through a range of emission wavelengths measuring relative fluorescence units. This continues for all the excitation wavelengths within a specified range. In certain embodiments, the excitation wavelengths are within a range of from about 100 nm to about 1000 nm, or from about 200 nm to about 900 nm, or from about 250 nm to about 850 nm. The instrument determines the fluorescence from the nanoparticle by normalizing to the emission fluorescence of a blank sample (solution without nanoparticle). A two-dimensional plot of the excitation versus emission is obtained, which is observed as a colored contour plot displaying a crosshair at the maximum fluorescence intensity. Once the scans are complete, the sample is removed from the device.

The data generated by the scans is used to determine an intersect between the excitation and emission wavelengths yielding the highest fluorescence intensity. In certain embodiments, the data generated by the scans can be presented in the form of a "heat map" with excitation and emission wavelengths making up a Cartesian coordinate system. The intersect comprises the coordinates for the excitation and emission wavelengths at the point of highest fluorescence intensity. It has been discovered that this intersect can be indicative of various properties of the scanned nanoparticle complex. For example, the presence of an attached organic species on the nanoparticle affects the nanoparticle's fluorescent "fingerprint" thus providing information regarding whether the organic species is indeed attached to the nanoparticle. In addition to merely confirming the attachment of the organic species, the intersect can also provide information regarding the amount of the organic species that is attached to the nanoparticle. For example, certain embodiments according to the present invention can be utilized to determine the loading of a polymer coating onto the nanoparticle. Further yet, the intersect can also provide information regarding structural changes made to the organic species or biomolecule that occurred as a result of attachment to the nanoparticle that may effect the performance or function of the organic species or biomolecule, which is essential for drug delivery. Still further, when the sample is scanned over a wide range of wavelengths, the presence or absence of unknown species in the sample, such as potential contaminants, can be identified.

Typically, the intersect is compared with to one or more know standard for the nanoparticle and/or nanoparticle complex in order to obtain confirmation of the attachment of the organic species, quantify the amount of organic species attached, or identifying structural changes made to the organic species during attachment to the nanoparticle. In certain embodiments, the standards are prepared by performing scans similar to those performed on the sample, but the standards have been "confirmed" via traditional means, such as those discussed previously. Once a set of standards have been prepared, comparison of the intersects of tested samples and characterization of the nanoparticles or nanoparticle complexes is straightforward and can be accomplished directly. In particular embodiments, the standards may comprise the intersects for the nanoparticle only, the nanoparticle complex with known quantities of organic species attached, and the nanoparticle complex with organic species of a particular structure. In one particular embodiment, retention of the intended complex and quantification of the payload can be performed substantially simultaneously. In this embodiment, a standard curve of nanoparticle fluorescence intensity versus nanoparticle concentration is initially generated. The excitation and emission wavelengths can then be used to verify retention of the intended nanoparticle complex, and the fluorescence intensity can be used to quantify the amount of organic species that has been attached to the nanoparticle.

EXAMPLES

The following examples describe 2D-FDS analyses conducted on nanoparticles having various biomolecules attached thereto. It is noted that these analyses are exemplary in nature and should not be taken as being limiting of the scope of the present invention.

Example 1

In this example, 2D-FDS was used to illustrate how two proteins, Luciferase and b-Galactosidase, interact with zinc oxide nanoparticles (ZnO-NP). Particularly, the shift in the excitation and emission wavelength intersect resulting from attachment of the proteins as compared to the uncomplexed nanoparticles was observed.

Dry powders of nanomaterials were weighed out in milligram quantities and suspended in spectral grade water. Once suspended at the intended concentration (mg/mL), the nanoparticles were ultra-sonicated to evenly disperse the particles throughout the solution. The nanoparticles were transferred to a black 96 well microplate at a volume of 200 µL, and the plate was inserted into a Spectramax i3x 2D-FDS instrument from Molecular Devices. This spectrophotometer (instrument) utilizes Softmax Pro 6.4.2 software to specify the measurement parameters. To generate the 2D-FDS data, the settings were adjusted to detect fluorescence of unknown wavelengths. The spectra optimization wizard was prompted upon reading the sample, where the range of excitation and emission wavelengths to scan were inserted, as well as the intervals or steps of measurement. The read height was set to 1 mm from the top of the plate. The instrument reads only one sample at a time. For each excitation wavelength, the instrument consecutively scans through a range of emission wavelengths measuring relative fluorescence units. This continues for all the excitation wavelengths specified in the range. The instrument determines the fluorescence from the nanoparticle by normalizing to the emission fluorescence of the blank sample (solution without nanoparticle). Finally, a two-dimensional plot of the excitation versus emission is obtained, which is observed as a colored contour plot displaying the crosshair at the maximum fluorescence intensity.

Figure 1B:
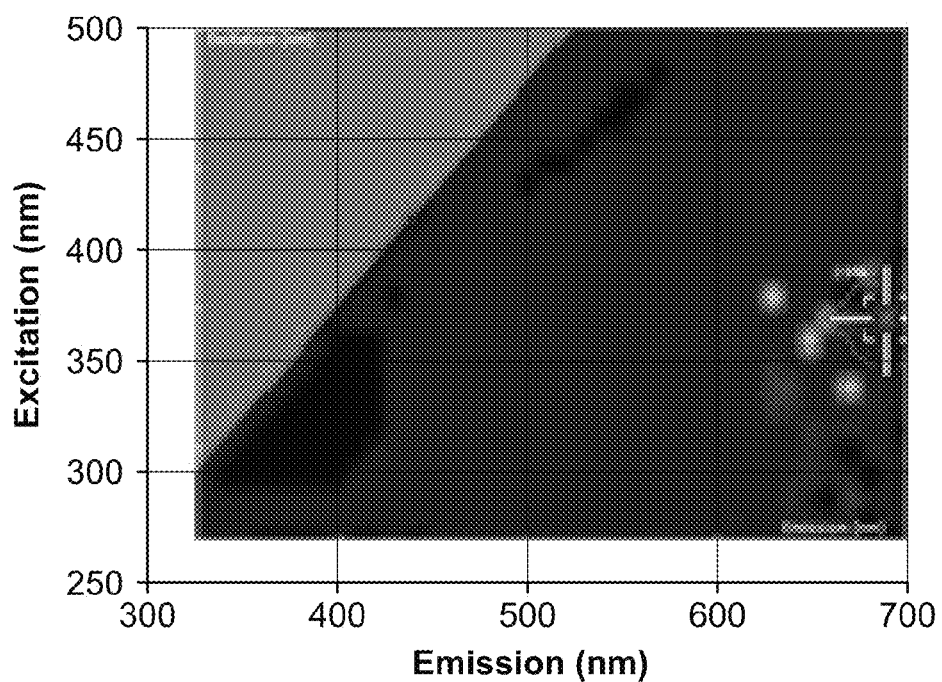
FIG. 1b is a 2D-FDS heat map for a ZnO/Luciferase nanoparticle complex.
Figure 1C:
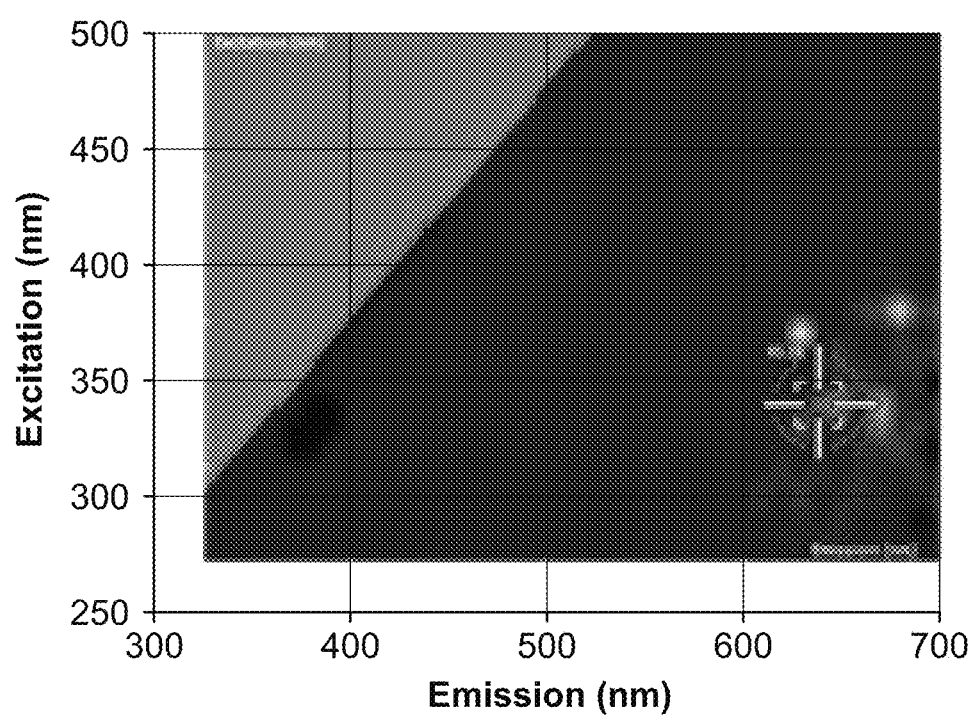
FIG. 1c is a 2D-FDS heat map for a ZnO/b-Galactosidase nanoparticle complex.

FIG. 1a illustrates an exemplary 2D-FDS heat map for ZnO-NP, FIG. 1b illustrates a heat map for ZnO-NP and Luciferase, and FIG. 1c illustrates a heat map for ZnO-NP and b-Galactosidase. Table 1 summarizes the optimized peak of each sample, with the data of the first trial followed by the second trial.

TABLE 1

| Sample | Optimized peak excitation (nm) | Optimized peak emission (nm) | Peak intensity ((S − B)/B) |
|---|---|---|---|
| ZnO NP | 350/360 | 660/630 | 278,600/263,00 |
| ZnO NP + Luc | 380/370 | 660/690 | 537,000/194,000 |
| ZnO NP + β-Gal | 330/340 | 660/640 | 67,900/95,100 |

As can be seen from FIGS. 1a-1c, the presence of protein molecules attached to the ZnO nanoparticle affected the fluorescence characteristics of the nanoparticle complex, which was readily discernible by 2D-FDS.

Example 2

Figure 2A:
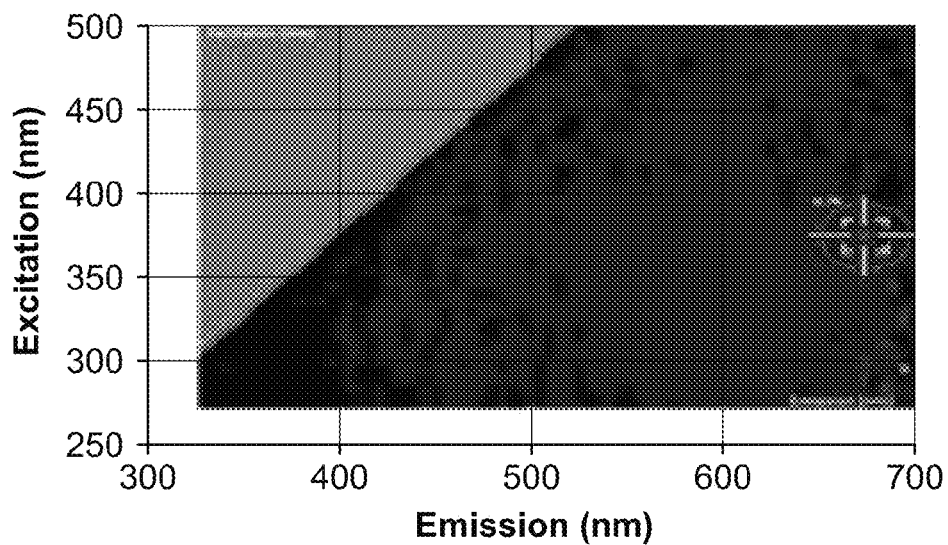
FIG. 2a is a 2D-FDS heat map for CoZnO composite.
Figure 2B:
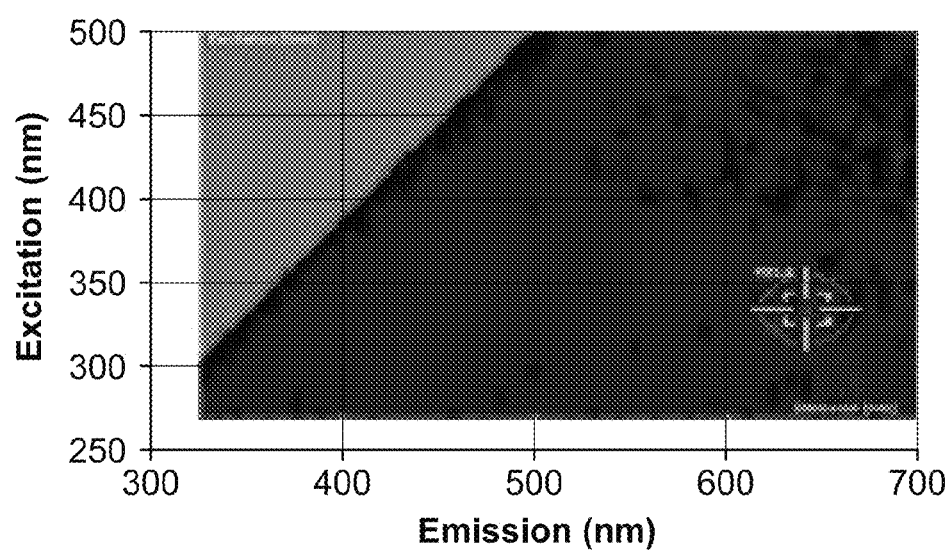
FIG. 2b is a 2D-FDS heat map for CoZnO with polyinosinic-polycytidylic acid (poly I:C) RNA nanoparticle complex.

In this example, 2D-FDS was used to illustrate the shift in the excitation and emission wavelength intersect between cobalt-zinc oxide (CoZnO) composite and CoZnO with polyinosinic-cytidylic acid (poly I:C) RNA attached. FIG. 2a illustrates the 2D-FDS excitation/emission optimum for ZnO—Co composite (375 nm/675 nm, RFU=1.7K). This optimum value shifts upon poly I:C RNA interaction (335 nm/685 nm, RFU=491) as shown in FIG. 2b. Thus, a shift in the optimal fluorescence intersect was identified when poly I:C RNA interacts with CoZnO nanoparticle composites. Decrease in fluorescence intensity, from 1.7K relative light units to 491, is another indication of interaction, as the fluorescence emitted from the nanoparticle is quenched by the biomolecule loaded onto the surface.

Example 3

Figure 3A:
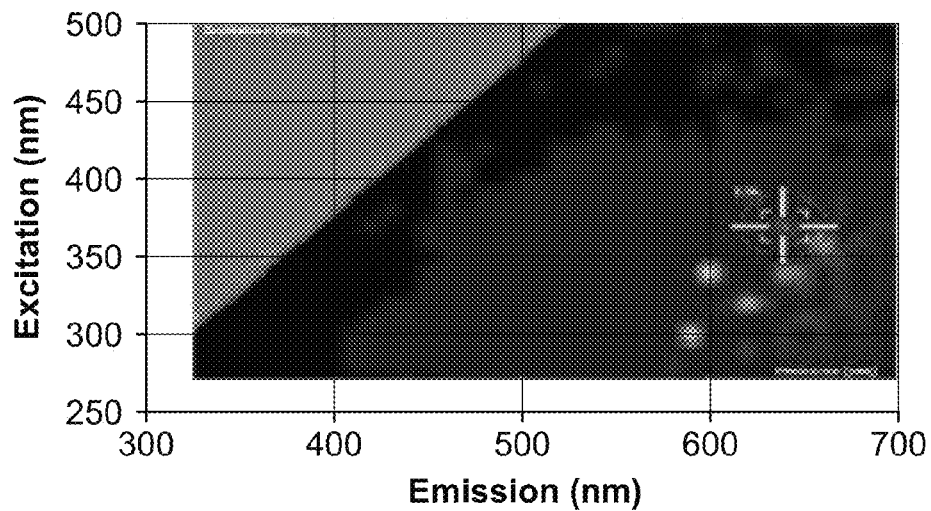
FIG. 3a is a 2D-FDS heat map for ZnO nanoparticle.
Figure 3B:
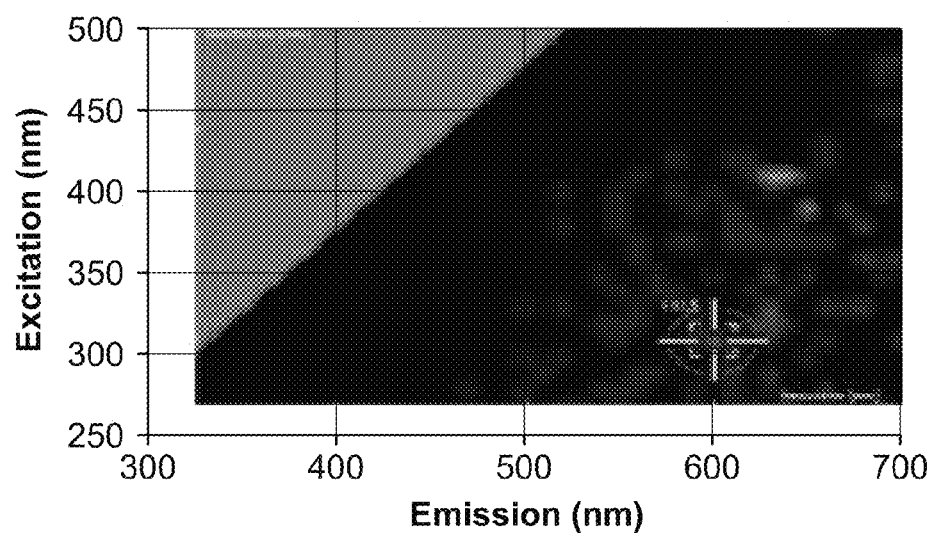
FIG. 3b is a 2D-FDS heat map for boron carbide ($B_4C$) nanoparticle.
Figure 3C:
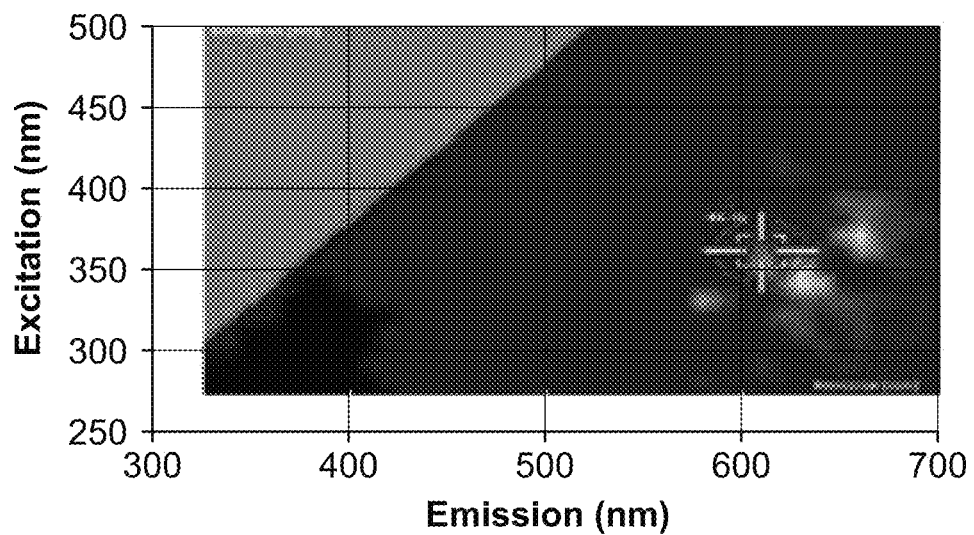
FIG. 3c is a 2D-FDS heat map for ZnO nanoparticle in the presence of protamine:poly I:C complex.
Figure 3D:
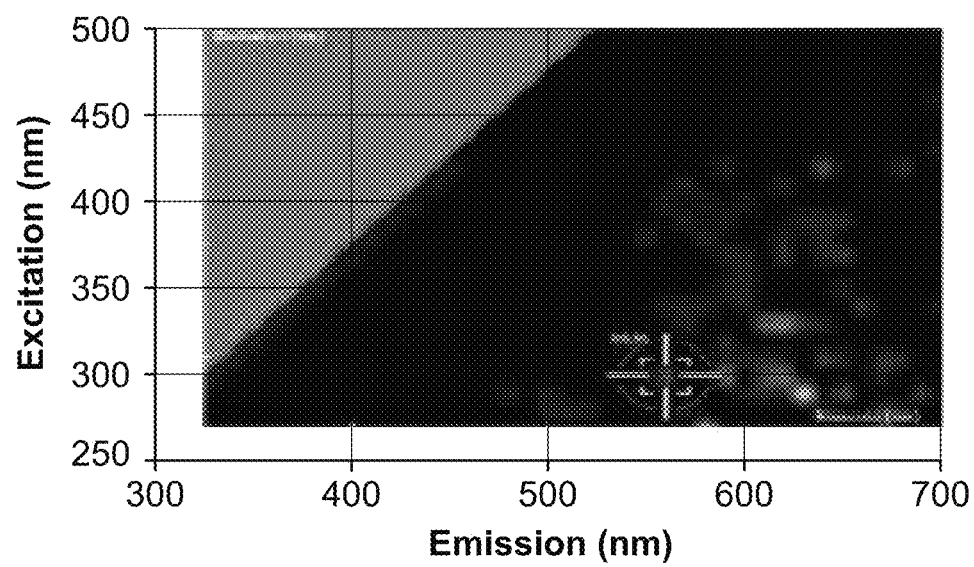
FIG. 3d is a 2D-FDS heat map for boron carbide ($B_4C$) nanoparticle in the presence of protamine:poly I:C complex.
Figure 3E:
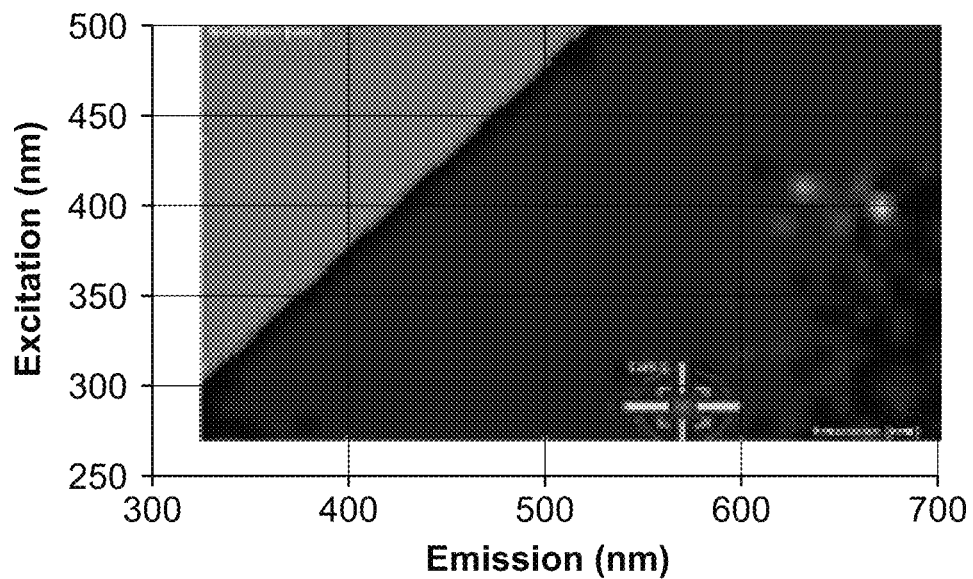
FIG. 3e is a 2D-FDS heat map for MgO nanoparticle.
Figure 3F:
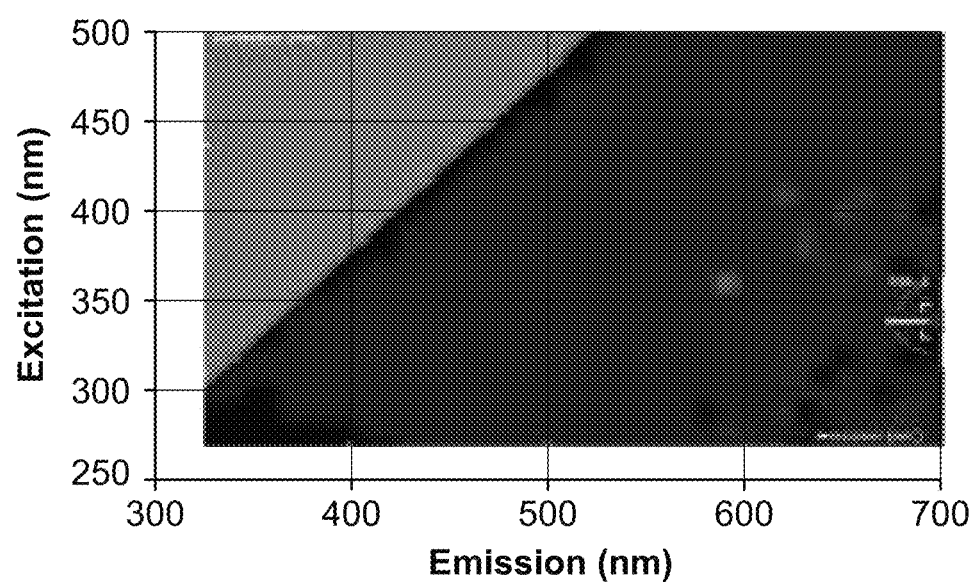
FIG. 3f is a 2D-FDS heat map for MgO nanoparticle in the presence of protamine:poly I:C complex.
Figure 3G:
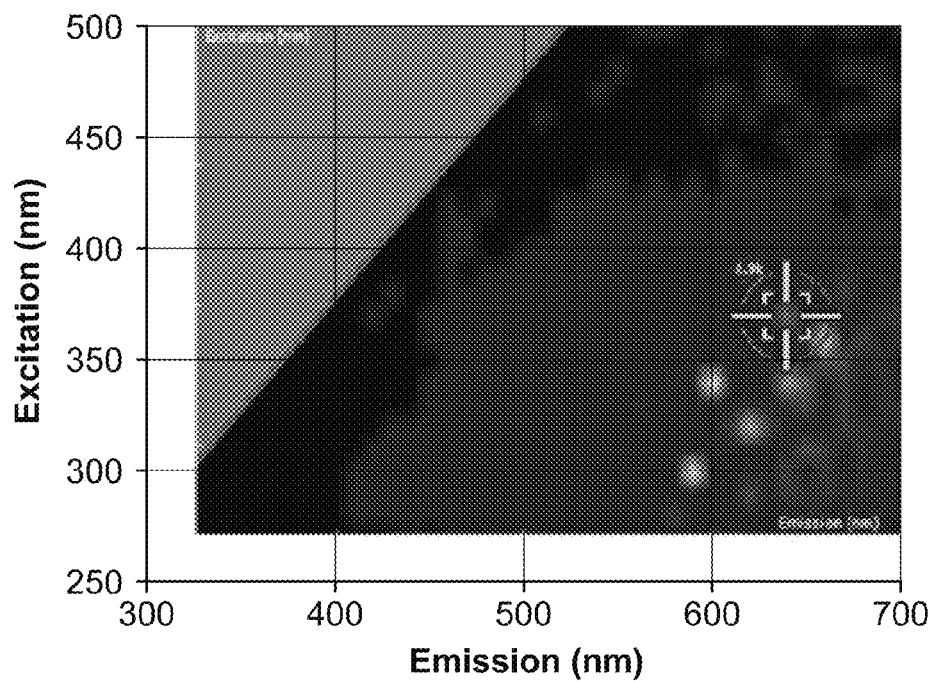
FIG. 3g is a 2D-FDS heat map for ZnO nanoparticle.
Figure 3H:
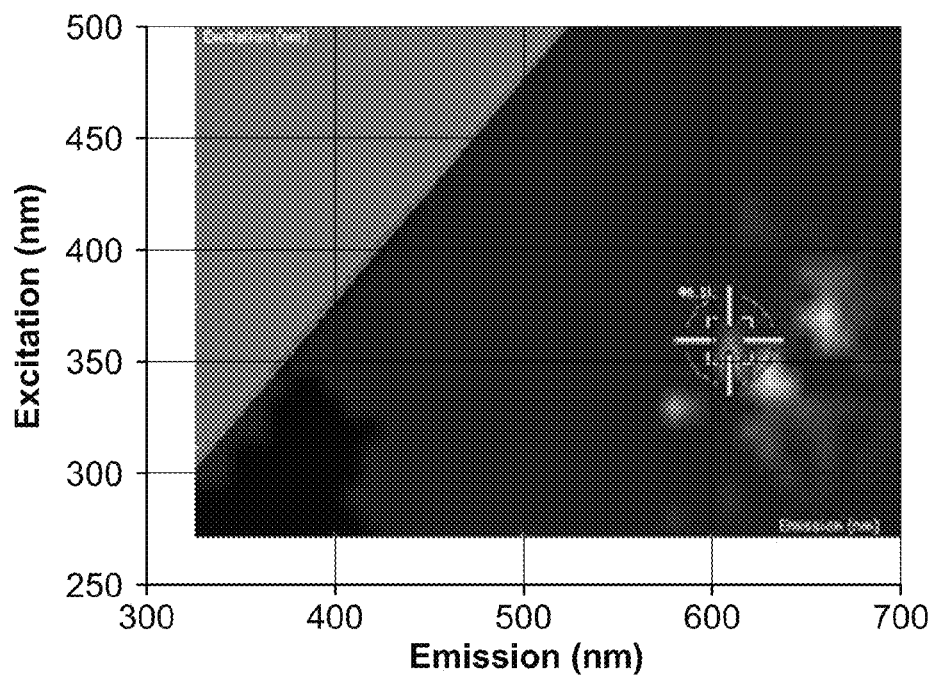
FIG. 3h is a 2D-FDS heat map for ZnO nanoparticle in the presence of protamine:poly I:C complex.

In this example 2D-FDS was used to illustrate the shift in the excitation and emission wavelength intersect between ZnO nanoparticle (FIG. 3a); ZnO nanoparticle in the presence of protamine:poly I:C complex (FIG. 3c); boron carbide ($B_4C$) nanoparticle (FIG. 3b); $B_4C$ nanoparticle in the presence of protamine:poly I:C complex (FIG. 3d); MgO nanoparticle (FIG. 3e); and MgO nanoparticle in the presence of protamine:poly I:C complex (FIG. 3f). As can be seen FIGS. 3a-f, the optimum excitation/emission intersect is different between the various material pairs. This example again confirms the utility of 2D-FDS as a rapid and sensitive means of quantifying biomolecular interaction with the nanoparticle. This example further illustrate how the peak position shifts and becomes more intense when ZnO nanoparticle (FIG. 3g) interacts with protein:RNA complex (protamine:poly I:C complex) (FIG. 3h).

Example 4

Figure 4A:
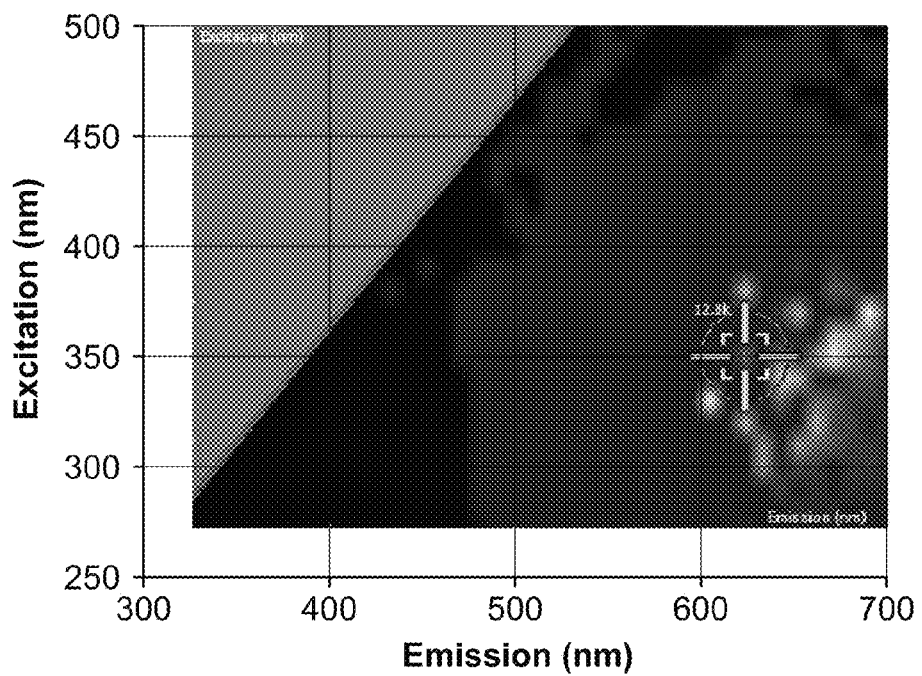
FIG. 4a is a 2D-FDS heat map for ZnO nanoparticle.
Figure 4B:
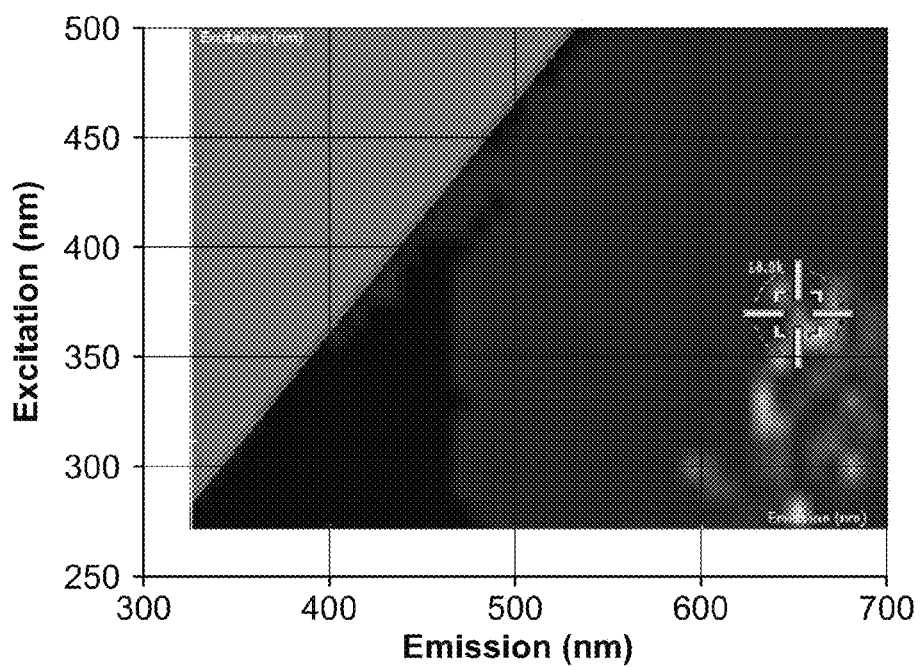
FIG. 4b is a 2D-FDS heat map for ZnO nanoparticle coated with polyethylene glycol.
Figure 4C:
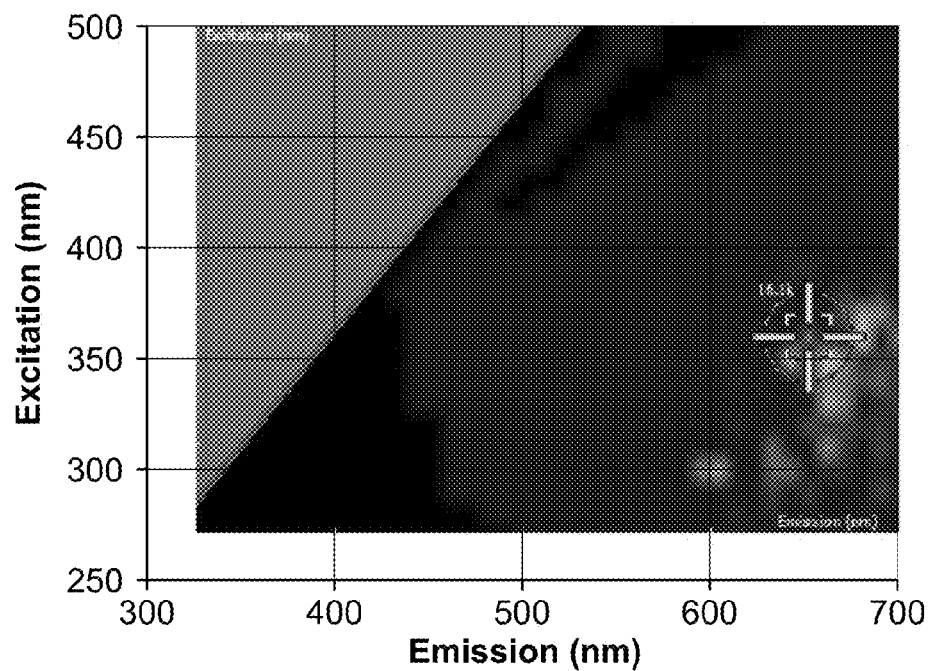
FIG. 4c is a 2D-FDS heat map for ZnO nanoparticle coated with glycol chitosan.
Figure 4D:
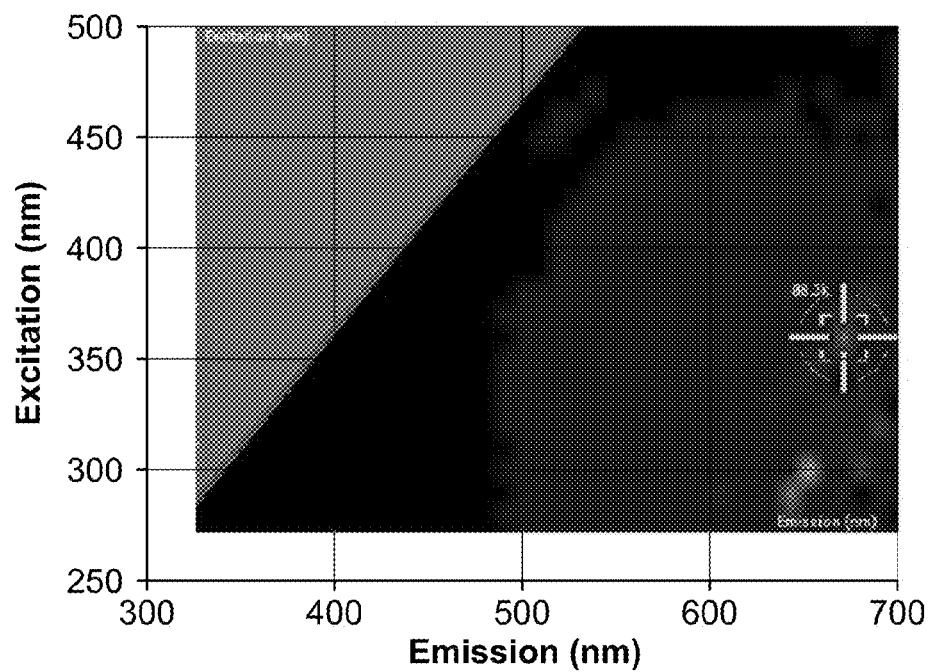
FIG. 4d is a 2D-FDS heat map for ZnO nanoparticle coated with polyacrylic acid.

In this example 2D-FDS was used to illustrate the shift in the excitation and emission wavelength intersect between ZnO nanoparticle and ZnO nanoparticle having a polymer coating applied thereto. All samples tested comprised a ZnO nanoparticle suspension having a concentration of 0.5 mg/mL. Those samples further comprising a polymer coating, the polymer was present in the suspension at a level of 0.1 mg/mL. FIG. 4a depicts a heat map for the ZnO nanoparticle suspension. FIG. 4b depicts a heat map for a polyethylene glycol-coated ZnO nanoparticle suspension. FIG. 4c depicts a heat map for a glycol chitosan-coated ZnO nanoparticle suspension. FIG. 4d depicts a heat map for a polyacrylic acid-coated ZnO nanoparticle suspension. The excitation wavelength, emission wavelength, and peak intensity data for the tests are provided in Table 2. Note that for certain samples, the scans were repeated and certain parameters are expressed in terms of the range of values observed. As can be seen, the presence of the various polymer coatings affected the 2D-FDS fingerprint for the nanoparticle complex.

TABLE 2

| Nanomaterial | Excitation λ (nm) | Emission λ (nm) | Intensity (RFU) |
|---|---|---|---|
| ZnO-NP | 350 | 620 | 12.8K |
| ZnO + mPEG | 370 | 610-650 | 16.5K-28.8K |
| ZnO + Glycol Chitosan | 340-360 | 650-690 | 16.1K-36.3K |
| ZnO + PAA | 340-360 | 660-670 | 54.2K-88.3K |

Example 5

In this example, 2D-FDS is demonstrated as a method to identify nanomaterials and confirm complexation with molecules following surface functionalization or biomolecule loading.

Materials

Commercial zinc oxide nanoparticles (ZnO NP) and HPLC grade water were purchased from Sigma Aldrich (St. Louis, Mo., USA). Iron oxide nanoparticles (Fe2O3 NP) were obtained from Plasma Chem (Berlin, Germany). Nickel oxide nanoparticles (NiO NP) were synthesized by Dr. K. Ghosh (Missouri State University, Springfield, Mo., USA). ZnO NP synthesized by microwave irradiation methods by G. Glaspell. ZnO nanobelts were synthesized as previously reported by Gann, H. et al., Interaction of MnO and ZnO Nanomaterials with Biomedically Important Proteins and Cells. J. Biomed. Nanotechnol. 6, 37-42 (2010). Glycol chitosan was obtained from MP Biochemicals. Poly acrylic acid (PAA), methoxy polyethylene glycol 5000 (mPEG 5000), torula yeast RNA (TYRNA), and polyinosinic: polycytidylic acid (pIC) were purchased from Sigma Aldrich. Splice switching oligonucleotide (SSO) was synthesized by Trilink Biotechnologies (San Diego, Calif., USA). The 623 SSO sequence (5'-GTT ATT CTT TAG AAT GGT GC-3') was modified with a phosphothioate backbone and 2'-O Methyl groups. Ras-Binding domain (RBD) was purchased from EMD Millipore. Samples were read in a black 96 well microplate (Midsci).

Nanoparticles were weighed out at 1-2 mg and suspended in 1 mL of HPLC grade water in sterile microcentrifuge tubes. The particles were dispersed for 5 minutes at 50% amplitude and 20 seconds pulses using Sonics Vibracell VCX130 probe ultra-sonicator. For nanoparticle only samples, a concentration of 1 mg/mL or 0.5 mg/mL was scanned at a volume of 200 μL in a black 96 well plate. For surface functionalization studies, a concentration of 1 mg/mL nanoparticle was incubated with 0.1 mg/mL polymer, either glycol chitosan, PAA, or mPEG, for 30 minutes at room temperature on an orbital shaker set at 250 rpm prior to being transferred to a black 96 well plate. For RNA loading experiments, 1 mg/mL nanoparticle was incubated with 0.1 mg/mL RNA, either TYRNA, pIC, or SSO, on the orbital shaker set to 250 rpm for 30 minutes while on ice then transferred to a black 96 well plate. For RBD studies, the nanoparticle was diluted to a concentration of 0.5 mg/mL, and RBD concentrations included 50 μg/mL, 37.5 μg/mL, and 25 μg/mL. The nanoparticle and protein were incubated for 30 minutes on the orbital shaker set to 250 rpm at room temperature then transferred to a black 96 well plate. Microplates were scanned using the Molecular Devices Spectramax i3x spectrophotometer utilizing the Spectral Optimization Wizard as part of Softmax Pro 6.4.2 software (Sunnyvale, Calif., USA). Settings were specified to read fluorescence end point of unknown wavelengths, prompting the Spectral Optimization Wizard. The range of excitation and emission wavelengths to scan was inputted as 250-500 nm and 280-700 nm, respectively. Read height (from the top of the microplate) was set to 1 mm, and 5 or 10 nm wavelength increments were selected. The flash lamp was set to 6 pulses, where the values for each excitation and emission intersect were averaged between 6 readings. The software inherently analyzes the data using the equation: $(S-B)/B$ where the difference between the sample and background readings were divided by the background.

Results

Figure 5:
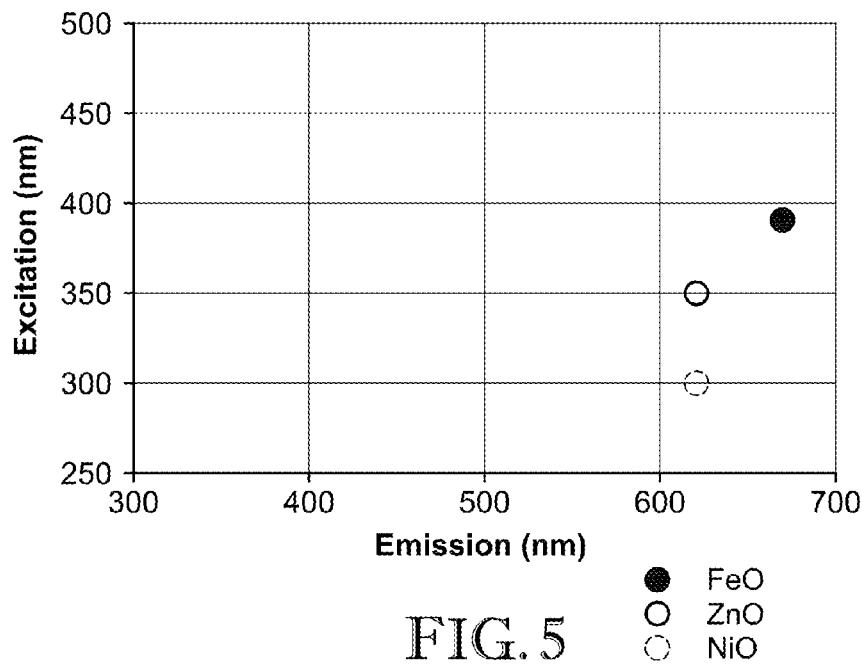
FIG. 5 is a comparative plot of excitation and emission wavelengths at peak intensity for ZnO, $Fe_2O_3$, and NiO nanoparticles.

Zinc oxide (ZnO) is an indigenously fluorescent material that is of interest due to its wide range of conductivity and its applications for electronic and photonic modalities. ZnO has a wide band gap energy of 3.37 eV, which calculates to 375 nm as the start of emission. Due to the Stoke's shift phenomenon, the optimal excitation wavelength of ZnO is between 325-350 nm. ZnO exhibited an optimal excitation and emission intersect of 350 nm and 620 nm, respectively, with a fluorescent intensity of 12,800 light units. Iron oxide ($Fe_2O_3$) is predominantly exploited for its magnetic properties and its high thermodynamic stability. Direct electron transitions for hematite ($\alpha$-$Fe_2O_3$) can be observed at the band gap energies of 3.0-4.7 eV, which corresponds to a range of excitable wavelengths from 215-390 nm. $Fe_2O_3$ gives an optimal excitation wavelength of 390 nm with emission at 670 nm and a fluorescent intensity of 176.3 light units. Nickel oxide (NiO) nanocrystals were shown to have a band gap energy of 3.62 eV. This exciton ground state energy corresponds to a range of wavelengths from 290-315 nm. NiO gives a spectral signature showing optimal excitation at 300 nm with an emission at 620 nm and a fluorescent intensity of 6,000 light units. Evaluating the optimal excitation and emission intersects for the three nanomaterials revealed that this technique is specific to a material's elemental composition and dependent upon the band gap energy within the material. The unique spectral signatures can be seen on the comparative plot of the three nanoparticles in FIG. 5.

Figure 6:
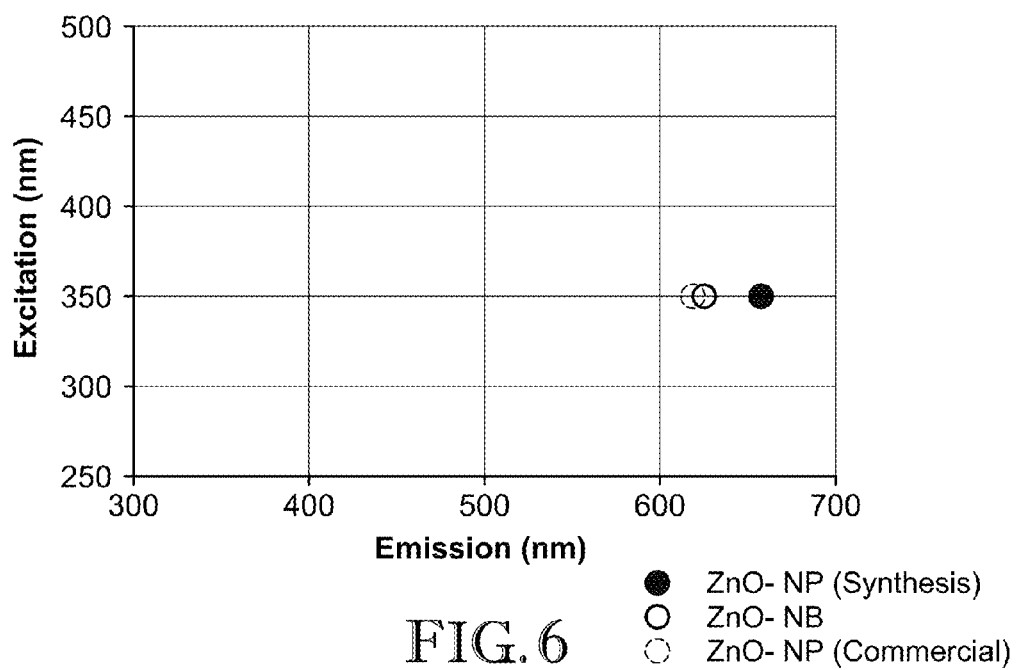
FIG. 6 is a comparative plot of excitation and emission wavelengths at peak intensity for various forms of ZnO.

To further explore how this technique can be applied to characterize nanomaterials, two types of ZnO nanoparticles differing in surface properties were tested, where one was derived commercially and the other synthesized by microwave irradiation (M.I.) method. These nanoparticles were compared to ZnO nanobelts, or long filamentous nanostructures, to observe the effects of morphology on the spectral signature. The synthesized ZnO NP gave an optimal excitation and emission intersect at 350 and 660 nm with an intensity of 263,000 light units. The commercial ZnO NP yielded an identical excitation of 350 nm and emission at 620 nm. The fluorescent intensity of the commercial ZnO NP is twice that of the synthesized ZnO NP at 567,000 light units. ZnO nanobelts gave an optimal excitation and emission intersect of 350 nm and 625 nm with a fluorescent intensity of 16,400 light units. As shown in FIG. 6, it is evident that the excitation wavelength reflects the materials composition. However, the emission wavelength differs between the two ZnO nanoparticles resulting from differences in surface electronic properties. The fluorescent intensity of the three ZnO nanomaterials differ significantly, revealing that synthesis as well as morphology play largely into optimizing the fluorescent signal of the nanoparticle for detection.

Figure 7:
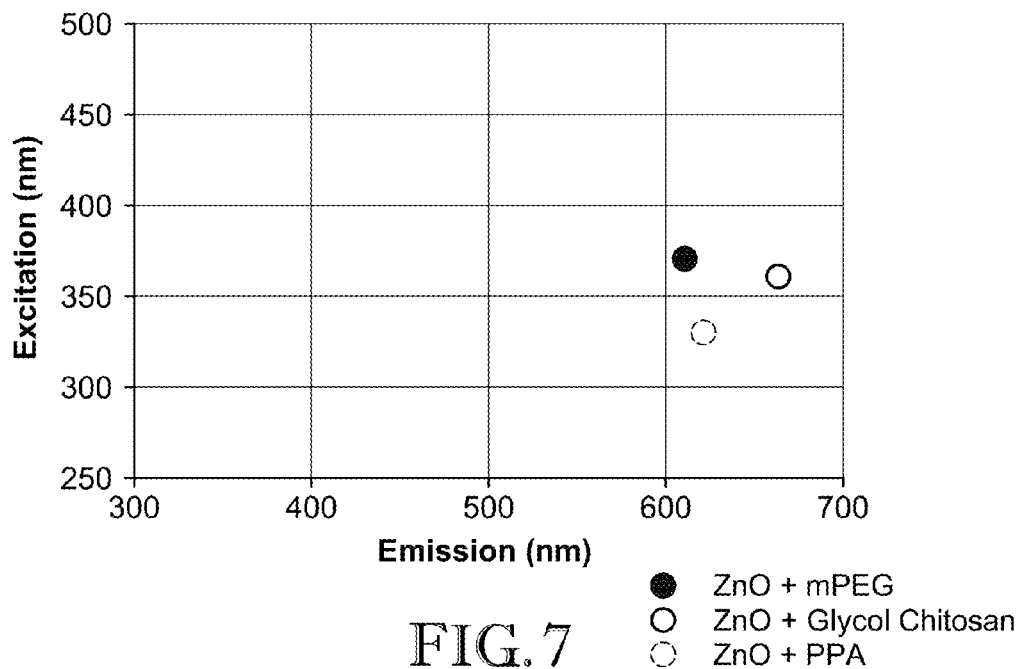
FIG. 7 is a comparative plot of excitation and emission wavelengths at peak intensity showing spectral signature shift upon surface functionalization of zinc oxide (ZnO) as a result of polymer association.

Nanoparticles offer a high surface area to volume ratio making them ideal delivery agents and prone to surface functionalization. With such vast applications of creating complex nanocarriers housing multiple molecules, 2D-FDS lends itself to confirm complexation through detection of changes in the fluorescent signature. ZnO NP gave an optimal excitation and emission intersect of 350 nm and 620 nm with a fluorescent intensity of 567,000 light units. This optimal intersect shifted upon addition of ZnO NP binding polymers: glycol chitosan, polyacrylic acid (PAA), and methoxy polyethylene glycol (mPEG). Glycol chitosan is of interest due to its biocompatibility and biodegradability, as well as the ability to covalently link biomolecules to the amine groups that derive its backbone. In the presence of glycol chitosan, the spectral signature shifted to 360 nm and 660 nm, respectively. Fluorescent quenching was observed upon interaction with glycol chitosan, diminishing the intensity by over 530,000 light units. PAA has been used to prevent nanoparticle aggregation and serves as a platform to electrostatically load biomolecules. In the presence of PAA, an excitation shift to 330 nm was observed, with the emission wavelength remaining unchanged at 620 nm. Again there was significant fluorescent quenching indicative of interaction with a difference of 549,000 light units. As a copolymer nanoparticle, mPEG has been used to encapsulate therapeutics, offering a slow release, while maintaining particle stability in vivo. With an even greater decrease in intensity, mPEG showed a shift in excitation to 370 nm and a minor shift in emission to 610 nm. A comparative plot is given in FIG. 7 revealing three distinct shifts in the spectral signature of ZnO NP per polymer.

Figure 8:
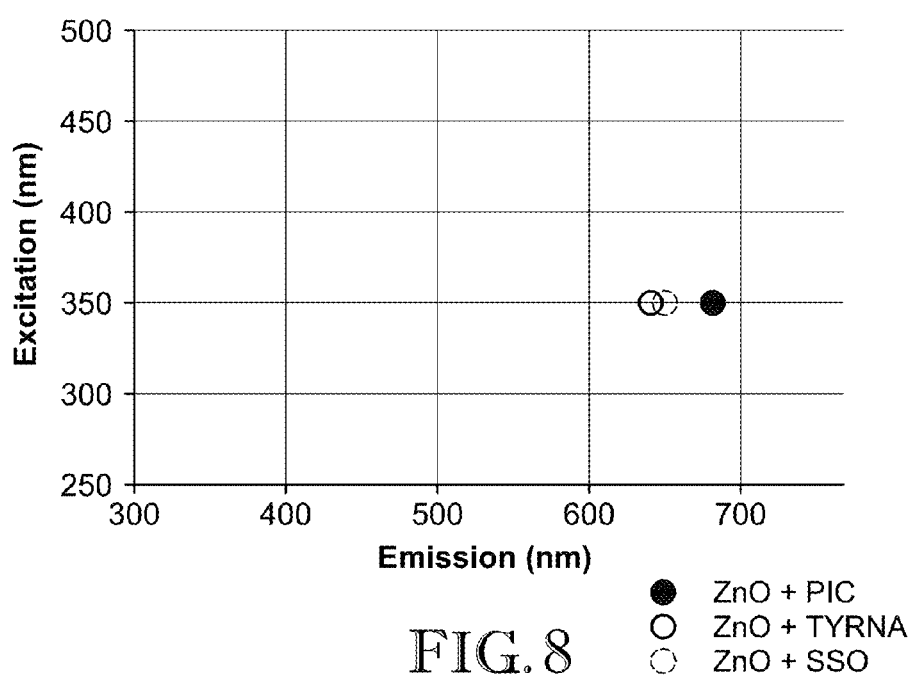
FIG. 8 is a comparative plot of excitation and emission wavelengths at peak intensity showing spectral signature shift upon RNA loading onto zinc oxide (ZnO) nanoparticle.

Surface functionalization of nanoparticles is not limited to chemicals and synthetic compounds, but rather a large aim of biomedical nanotechnology focuses on the loading of biomolecules including protein, DNA, and RNA onto nanoparticles. Typically RNA cannot be detected by fluorescence spectroscopy without the aid of a dye; however, 2D-FDS can further be used to detect successful RNA adsorption to the nanoparticle surface. Compared to the spectral signature of ZnO NP, a shift was observed in the optimal emission wavelength of three RNAs. RNA derived from Torula yeast (TYRNA) was used as a model of RNA found naturally in the biological environment. Upon binding ZnO NP, a shift in the emission of the spectral signature was observed at 640 nm, while the excitation wavelength remains unchanged. Dendrimer and nanoparticle-mediated delivery of splice-switching oligonucleotides (SSOs) as a means to test the RNA functionality upon transport into the cell has been previously reported. A shift in the optimal emission wavelength, to 650 nm, was observed when ZnO NP binds SSO, while excitation remained unaltered. Polyinosinic-polycytidylic acid (pIC) is a double stranded RNA that initiates an innate immune response by binding the intracellular receptor, toll-like receptor 3 (TLR3). pIC inhibits tumor growth by recruiting mature dendritic cells to the tumor site, overcoming immunosurveillance evasion. There is a large interest in the scientific community in loading vaccine adjuvants onto nanoparticles; therefore, pIC was chosen representatively. The greatest shift in emission was observed for pIC to 680 nm. A comparative plot is given in FIG. 8, where ZnO NP bound to TYRNA and SSO nearly overlap in the shifted spectral signature, and pIC bound to ZnO NP was shown to have the greatest shift. Dynamic fluorescent quenching is observed suggesting complexation as the intensity decreased from 12,800 light units of ZnO NP alone to 2,300-7,200 light units in the presence of RNA. This is consistent with the direct RNA interaction to ZnO NP as evidenced by Raman spectroscopy.

Figure 9:
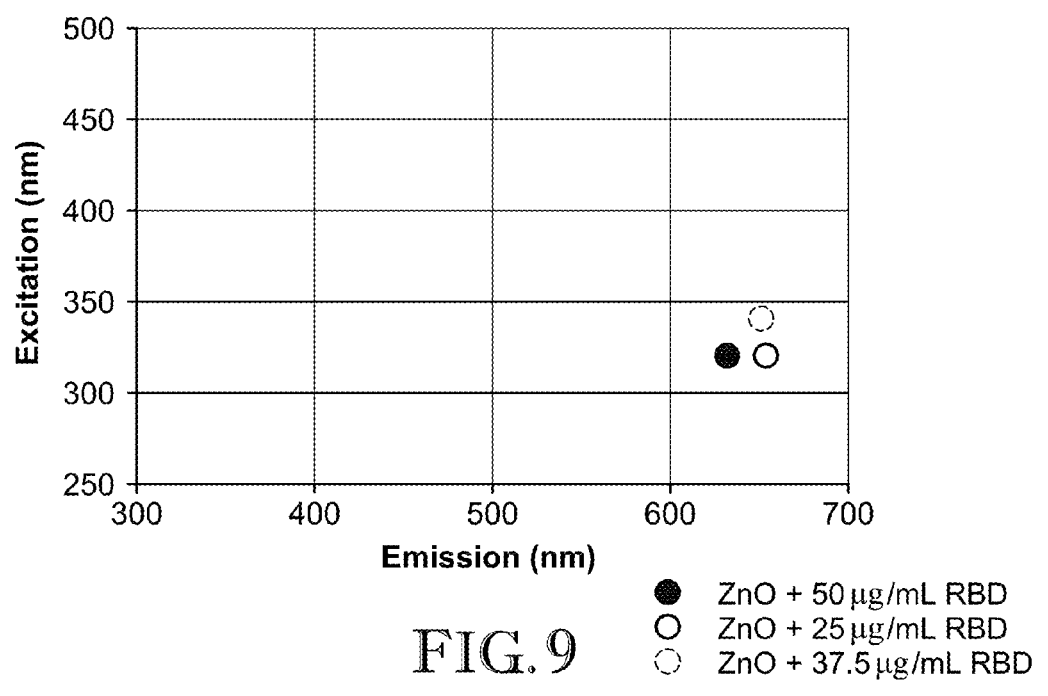

2D-FDS can be used to detect protein interactions at the nanoparticle surface. Ras-Binding domain (RBD) contains the first 149 residues of C-Raf-1 protein which binds Ras-GTP, a known cancer target, as a downstream effector. RBD was loaded onto ZnO NP at three concentrations: 50 µg/mL, 37.5 µg/mL, and 25 µg/mL. Compared to ZnO NP, a shift in excitation and emission, from 350 nm and 620 nm respectively, was observed for the three spectral scans. At 50 µg/mL RBD, the excitation shifted to 320 nm and the emission shifted to 630 nm. This concentration revealed the greatest fluorescent quenching from 12,800 relative light units to 3,100 light units. At 37.5 µg/mL RBD, the spectral signature of ZnO NP shifted to a different excitation and emission intersect, 340 nm and 650 nm, respectively. Fluorescent quenching was observed, to a lesser extent, with relative light units of 6,800. At 25 µg/mL RBD, the excitation shifted to 320 nm, and the emission shifted to 350 nm. At this concentration, fluorescent enhancement was observed increasing the relative light units to 19,000. A comparative plot is given in FIG. 9 revealing that excitation shifted towards the ultra-violet end of the spectrum and emission increased towards the infrared end of the spectrum upon interaction of the protein.

All values obtained from the spectral signatures shown in this Example are listed in Table 3. ZnO NP gives the highest fluorescent intensities (12,800-567,000 RLU) compared to other nanomaterials. Interaction of a polymer, RNA, or protein at the nanoparticle surface caused a decrease in the intensity and a shift in the excitation (320-370 nm) and emission (610-680 nm).

TABLE 3

| Sample | Excitation (nm) | Emission (nm) | Intensity (RFU) |
|---|---|---|---|
| ZnO NP (Commercial, 0.5 mg/mL) | 350 | 620 | 12,800 |
| Fe$_2$O$_3$ NP | 390 | 670 | 176.3 |
| NiO NP | 300 | 620 | 6,000 |
| ZnO NP (M.I. Synthesis) | 350 | 660 | 263,000 |
| ZnO NP (Commercial, 1 mg/mL) | 350 | 620 | 567,000 |
| ZnO NB | 350 | 625 | 16,400 |
| ZnO + Glycol Chitosan | 360 | 660 | 36,300 |
| ZnO + PAA | 330 | 620 | 18,000 |
| ZnO + mPEG | 370 | 610 | 16,500 |
| ZnO + TYRNA | 350 | 640 | 3,800 |
| ZnO + pIC | 350 | 680 | 2,300 |
| ZnO + SSO | 350 | 350 | 7,200 |
| ZnO + 50 µg/mL RBD | 320 | 630 | 3,100 |
| ZnO + 37.5 µg/mL RBD | 340 | 650 | 6,800 |
| ZnO + 25 µg/mL RBD | 320 | 650 | 19,000 |

Zinc oxide nanoparticle (ZnO NP), iron oxide nanoparticle (Fe2O3 NP), nickel oxide nanoparticle (NiO NP), microwave irradiation (M.I.), zinc oxide nanobelt (ZnO NB), polyacrylic acid (PAA), methoxy polyethylene glycol (mPEG), torula yeast RNA (TYRNA), polyinosinic: polycytidylic acid (pIC), splice switching oligonucleotide (SSO), Ras-Binding domain (RBD)

In conclusion, 2D-FDS generated a fluorescent signature dependent upon material composition. Three metal oxide nanoparticles, including zinc, iron, and nickel, are shown representatively; however, this technique could be used to determine the optimal fluorescent excitation and emission wavelengths for other nanomaterials and those derived from other polymeric or biomaterials.

2D-FDS can further discriminate between the surface properties of nanoparticles. It is known that heating and cooling cycles, along with differing the gaseous or solvent environment during synthesis, result in nanomaterials with varying surface properties. When comparing ZnO synthesized by microwave irradiation to commercial ZnO, a shift in emission was evident, which supports that the electronic properties at the nanomaterial surface change as a result of the synthesis process. However, no shift was evident when comparing ZnO nanobelts to commercial ZnO nanoparticles. It is suspected that particle morphology may have an effect on the spectral signature of ZnO nanomaterials. However, this data supports the conclusion that the optimal fluorescent excitation and emission intersect generated by 2D-FDS is a result of the material composition. Comparing commercial ZnO NP at two concentrations, 0.5 and 1 mg/mL, shows a significant decrease in fluorescence from 567,000 light units to 12,800 light units. Therefore, it can be deduced that the fluorescent intensity of the nanomaterial is concentration dependent.

When considering surface functionalization of a nanoparticle, a shift in the excitation wavelength can often be negated as materials are excitable within a range of wavelengths. However, the emission wavelength is often fixed per excitation wavelength, meaning that changes in the emission wavelength are indicative of surface interactions between the nanoparticle and molecule. This could be due to energy transfer between the adjacent electron orbitals of the interacting molecules and the formation of intermediate band gap levels. However, when assessing the extent of fluorescent quenching, mPEG exhibited the greatest quenching followed by PAA and glycol chitosan. Because PAA exhibits no shift in emission and intermediate fluorescent quenching, it can be concluded that it minimally binds to ZnO NP. Similarly, mPEG reveals a minor emission shift and high fluorescent quenching, indicating interaction to ZnO NP. Glycol chitosan gives the greatest emission shift, but the least fluorescent quenching, indicating binding to ZnO NP by a different mechanism. Each polymer loaded onto ZnO NP gave a distinctive shift in the spectra which could be attributed to the type of interaction between the polymer and nanoparticle.

Assessing biomolecule loading onto the nanoparticle surface, it was shown that ZnO NP binds RNA specifically as TYRNA, pIC, and SSO each gave a unique shift. pIC bound ZnO NP with the highest affinity as it gave the greatest shift in emission and fluorescent quenching. SSO gave an intermediate emission shift, followed by TYRNA which shifted the least by 20 nm. The trend observed for fluorescent quenching (pIC>TYRNA>SSO) could be attributed to the RNA size and surface area coverage at the ZnO NP surface. SSO is a short 20 nucleotide single stranded RNA with a linear structure. TYRNA is a single stranded, long RNA molecule that undergoes complex tertiary folding similar to tRNA. pIC is double stranded polymer RNA with a helical structure similar to DNA. Therefore, pIC being the largest molecule quenched the greatest, and SSO being the smallest molecule quenched the least. The length and varying structures of the three RNAs chosen attributes to the differences in affinity for ZnO NP resulting in a unique shift.

ZnO NP loaded with three concentrations of RBD revealed that the excitation undergoes a blue shift and the emission undergoes a red shift upon interaction. This indicates that energy is lost to other forms such as vibration than to fluorescent emission of photons as the emission shifts to longer wavelengths. It can be further concluded that the fluorescent intensity given from 2D-FDS is inversely related to the concentration of protein interacting at the nanoparticles surface. The greater the protein quantity, the greater the quenching as more protein is present at the nanomaterial's surface. At small protein concentrations, fluorescent enhancement occurs as a result in the increase in oxygen vacancies at the nanoparticle's surface upon protein interaction, suggesting interaction with zinc.

Once the range of excitation and emission wavelengths are established for the nanomaterial of interest, surface functionalization and biomolecule loading onto the nanoparticle can further be detected by 2D-FDS. In the presence of the polymers or biomolecules, a distinct shift was observed in the spectral signature of ZnO NP per species and concentration loaded onto the particle. The greater the quenching of fluorescent intensity and the greater the shift in emission correlate with stronger binding. 2D-FDS is a novel technique that provides a larger understanding on the optical properties of nanoparticles, while validating interactions at the nanomaterials surface. 2D-FDS lends itself as a quality assurance tool that could be extended to other intrinsically fluorescent molecules.

We claim:

1. A method of detecting the attachment of an organic species onto the surface of one or more nanoparticles within a sample comprising the nanoparticles and the organic species, wherein the method comprises performing concurrent scans of the fluorescence excitation and emission wavelengths for the nanoparticles within the sample and determining an intersect between the excitation and emission wavelengths yielding the highest fluorescence intensity, the intersect indicating the presence or absence within the sample of a nanoparticle complex comprising the one or more nanoparticles having the organic species attached to the surface of the nanoparticle.

2. The method of claim 1, wherein the method further comprises comparing the intersect to one or more known standards for the nanoparticle and/or nanoparticle complex.

3. The method of claim 2, wherein the one or more known standards comprise the intersect between the excitation and emission wavelengths yielding the highest intensity for the nanoparticle without the organic species attached to the surface of the nanoparticle.

4. The method of claim 1, wherein the organic species comprises a member selected from the group consisting of proteins, protein enzymes, RNA, DNA, oligonucleotides, aptamers, pharmaceutical compounds, and combinations thereof.

5. The method of claim 4, wherein the organic species comprises a member selected from the group consisting of B-Galactosidase, Luciferase, reverse transcriptase enzymes, deoxyribonuclease, polyinosinic-polycytidylic acid RNA, RNAse, protamine sulfate, Ras binding domain (RBD) peptide, torula yeast RNA, splice switching oligonucleotide (SSO), polyethylene glycol (PEG), glycol chitosan, and polyacrylic acid (PAA).

6. The method of claim 1, wherein the organic species comprises a polymer.

7. The method of claim 6, wherein the polymer at least partially coats the surface of the nanoparticle.

8. The method of claim 1, wherein the concurrent scans of the fluorescence excitation and emission wavelengths for the nanoparticles are performed using two-dimensional fluorescence difference spectroscopy.

9. The method of claim 1, wherein the nanoparticle comprises a member selected from the group consisting of metal oxides, elemental metals, and combinations thereof.

10. The method of claim 9, wherein the nanoparticle is selected from the group consisting of the lanthanides, ZnO, ZnS doped Mn, ZnS doped Fe, MgO, MnO, CoO, $Si_3N_4$, CSi, $B_4C$, NiO, Ni/NiO, Ni/ZnO, Co/ZnO, Au, FeO, and $Fe_2O_3$.

11. A method of quantifying the attachment of an organic species onto the surface of one or more nanoparticles a nanoparticle complex, wherein the method comprises:
performing concurrent scans of the fluorescence excitation and emission wavelengths for the nanoparticle complex;
determining an intersect between the excitation and emission wavelengths yielding the highest fluorescence intensity; and
comparing the intersect to one or more known standards for the nanoparticle complex to determine an amount of the organic species that is attached to the nanoparticle.

12. The method of claim 11, wherein the concurrent scans of the fluorescence excitation and emission wavelengths for the nanoparticle complex are performed using two-dimensional fluorescence difference spectroscopy.

13. The method of claim 11, wherein the organic species comprises a member selected from the group consisting of proteins, protein enzymes, RNA, DNA, oligonucleotides, aptamers, pharmaceutical compounds, and combinations thereof.

14. The method of claim 13, wherein the organic species comprises a member selected from the group consisting of B-Galactosidase, Luciferase, reverse transcriptase enzymes, deoxyribonuclease, polyinosinic-polycytidylic acid RNA, RNAse, protamine sulfate, Ras binding domain (RBD) peptide, splice switching oligonucleotide (SSO), torula yeast RNA, polyethylene glycol (PEG), glycol chitosan, and polyacrylic acid (PAA).

15. The method of claim 11, wherein the organic species comprises a polymer.

16. The method of claim 15, wherein the polymer at least partially coats the surface of the nanoparticle.

17. The method of claim 11, wherein the nanoparticle comprises a member selected from the group consisting of metal oxides, elemental metals, and combinations thereof.

18. The method of claim 17, wherein the nanoparticle is selected from the group consisting of the lanthanides, ZnO, ZnS doped Mn, ZnS doped Fe, MgO, MnO, CoO, $Si_3N_4$, CSi, $B_4C$, NiO, Ni/NiO, Ni/ZnO, Co/ZnO, Au, FeO, and $Fe_2O_3$.

19. A method of detecting changes in the structure of a biomolecule associated with attachment of the biomolecule to a nanoparticle thereby forming a nanoparticle complex, wherein the method comprises:
performing concurrent scans of the fluorescence excitation and emission wavelengths for the nanoparticle complex;
determining the intersect between the excitation and emission wavelengths yielding the highest fluorescence intensity; and
comparing the intersect to one or more known standards for the nanoparticle complex to detect changes in the biomolecule structure occurring during attachment to the nanoparticle.

20. The method of claim 19, wherein the concurrent scans of the fluorescence excitation and emission wavelengths for the nanoparticle complex are performed using two-dimensional fluorescence difference spectroscopy.

21. The method of claim 19, wherein the biomolecule comprises a member selected from the group consisting of proteins, protein enzymes, RNA, DNA, oligonucleotides, aptamers, pharmaceutical compounds, and combinations thereof.

22. The method of claim 21, wherein the biomolecule comprises a member selected from the group consisting of B-Galactosidase, Luciferase, reverse transcriptase enzymes, deoxyribonuclease, polyinosinic-polycytidylic acid RNA, RNAse, protamine sulfate, Ras binding domain (RBD) peptide, splice switching oligonucleotide (SSO), torula yeast RNA, polyethylene glycol (PEG), glycol chitosan, and polyacrylic acid (PAA).

23. The method of claim 19, wherein the nanoparticle comprises a member selected from the group consisting of metal oxides, elemental metals, and combinations thereof.

24. The method of claim 23, wherein the nanoparticle is selected from the group consisting of the lanthanides, ZnO, ZnS doped Mn, ZnS doped Fe, MgO, MnO, CoO, $Si_3N_4$, CSi, $B_4C$, NiO, Ni/NiO, Ni/ZnO, Co/ZnO, Au, FeO, and $Fe_2O_3$.

* * * * *